US00PP33471P2

(12) United States Plant Patent
Korlipara

(10) Patent No.: US PP33,471 P2
(45) Date of Patent: Sep. 7, 2021

(54) ***ECHINACEA* PLANT NAMED 'TNECHSDL'**

(50) Latin Name: ***Echinacea* spp.**
Varietal Denomination: TNECHSDL

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 17/165,007

(22) Filed: Feb. 2, 2021

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

(56) References Cited

PUBLICATIONS https://www.perishablenews.com/floral/terra-nova-nurseries-introduces-sneak-peek-of-echinacea-sunny-days-lemon/; Mar. 9, 2020; 1 page.*

* cited by examiner

*Primary Examiner* — Kent L Bell
(74) *Attorney, Agent, or Firm* — Klarquist Sparkman, LLP

(57) ABSTRACT

A new and distinct *Echinacea* plant named 'TNECHSDL' characterized by enlarged disc florets forming an anemone-type inflorescence, bright yellow ray florets and yellow disc florets, ray florets which are held horizontally to drooping, a short, upright habit with excellent stem count, and excellent vigor.

2 Drawing Sheets

Botanical denomination: *Echinacea* spp.
Variety designation: 'TNECHSDL'.
Trademark designation: Sunny Days Lemon™.

BACKGROUND OF THE INVENTION

The present invention relates to a new and distinct cultivar of *Echinacea* and given the cultivar name 'TNECHSDL'. *Echinacea* is in the family Asteraceae. The new cultivar is part of a planned breeding program for a landscape series with compact habits and profuse, double inflorescences. The exact parents of this selection are unknown, unnamed, proprietary interspecific hybrids bred from *Echinacea paradoxa, Echinacea purpurea*, and *Echinacea tennesseensis.*

Compared to *Echinacea* 'TNECHCMY', U.S. Plant Pat. No. 31,142, the new cultivar is taller and more upright.

This new *Echinacea* cultivar is uniquely distinguished by:

1. enlarged disc florets forming an anemone-type inflorescence,
2. bright yellow ray florets and yellow disc florets,
3. ray florets which are held mostly horizontally to drooping,
4. a medium, upright habit with excellent stem count, and
5. excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding asexually propagations. The present invention has not been evaluated under all possible environmental conditions. The phenotype may vary with variations in environment without a change in the genotype of the plant.

DETAILED PLANT DESCRIPTION

Figure 1:
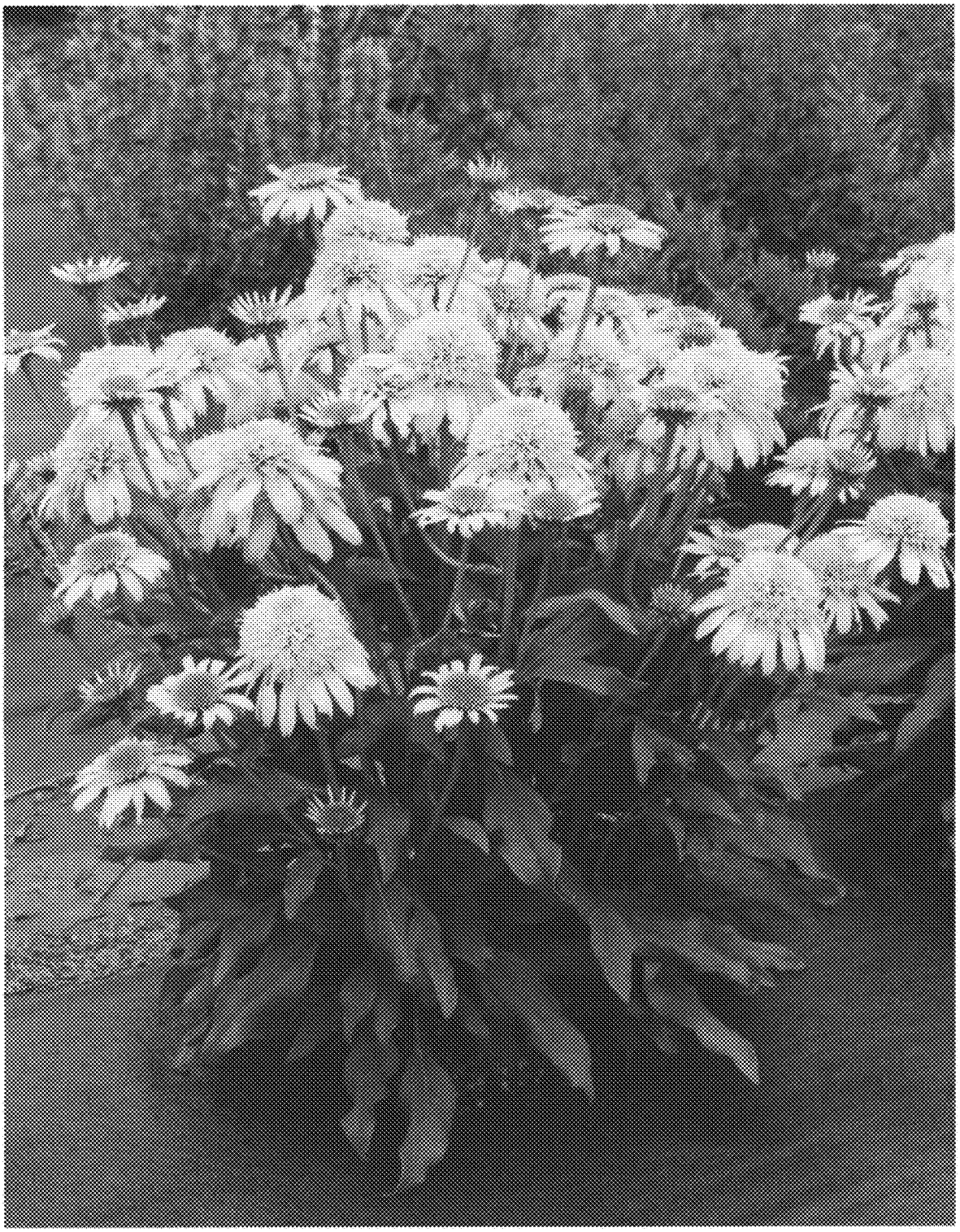
FIG. 1 shows a 17-month-old *Echinacea* 'TNECHSDL' growing in the trial field in full sun in late July in Canby, Oreg.
Figure 2:
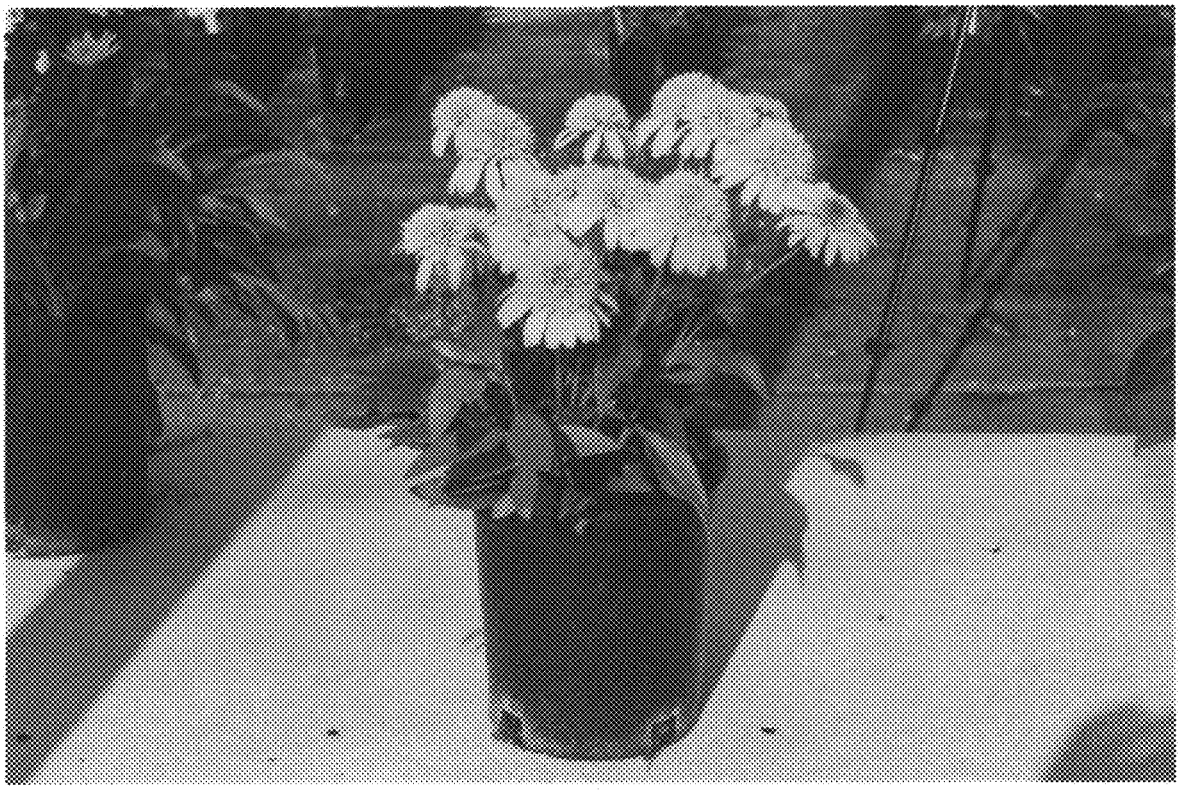
FIG. 2 shows a 7-month-old *Echinacea* 'TNECHSDL' grown in a 1 gallon container full sun in early August in Canby, Oreg.

The following is a detailed description of the new *Echinacea* cultivar based on observations of 17-month-old specimens growing in the trial bed in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart,* 5$^{th}$ edition.

Plant:

*Type.*—Herbaceous perennial.
*Hardiness.*—USDA Zones 4 to 9.
*Size.*—Grows to 40 cm wide and 45 cm tall to top of inflorescences.
*Form.*—Basal clump, with about 12 stems from the base.

*Vigor*.—Excellent.

*Roots*.—Fibrous, with many downward growing and few laterals, ivory in color, White Group NN155A, roots develop easily from cuttings from the crown.

Stem (flowering):

*Type*.—Ascending, with 1 to 9 inflorescences per stem.

*Size*.—To 40 cm tall to a terminal inflorescence and 6 mm wide at base.

*Strength*.—Excellent.

*Internode length*.—3 cm to 4 cm.

*Surface texture*.—Strigose.

*Rugosity*.—Absent.

*Variegation*.—Absent.

*Color*.—Yellow Green 146B.

Leaf (stem):

*Type*.—Simple.

*Shape*.—Lanceolate.

*Arrangement*.—Alternate, with about 15 leaves on the main stem.

*Blade size*.—Grows to 10 cm long and 3.4 cm wide.

*Margins*.—Sparsely serrate to entire.

*Apex*.—Acuminate.

*Base*.—Attenuate.

*Surface texture*.—Strigose on both sides.

*Rugosity*.—Absent.

*Venation*.—Pinnate, Greyed Green 193C on both sides.

*Variegation*.—Absent.

*Color*.—Topside Green N139B, bottom side closest to Yellow Green 147B.

*Petiole description*.—Clasping, grows to 4 cm long and 3 mm wide, scabrous, narrow leafy edges, both sides closest to Green 138A.

Inflorescence:

*Type*.—Composite on terminal stalked heads.

*Flowering stem*.—40 cm tall from the base of the plant to the terminal leaves below the peduncle; branched with 1 to 9 inflorescences per stem, diameter growing to 5 mm wide near the inflorescence; strigose; Yellow Green 146B.

*Peduncle*.—11.5 cm long from above terminal leaves to flower, 3.5 cm wide, strigose; Yellow Green 146C.

*Size*.—Grows to 8 cm wide and 6 cm deep as disc enlarges.

*Form*.—Ray florets held slightly down, reflexing more in older inflorescences, mature disc is rounded.

*Immature inflorescence* (*bud*).—2.6 cm wide and 1.6 cm deep, ray florets held mostly upright and rolled up so only the back color shows, between Yellow 3B and 3C, disc color Green 141B.

*Ray florets*.—Without pistil or stamen, to 15 in number, 53 mm long and 9 mm wide, oblanceolate with the tip two or three-toothed (each acute), teeth cut 2 mm to 8 mm deep, florets with entire margin, base attenuate, glabrous on both sides, horizontal to drooping attitude at origin; newly fully open florets topside Yellow 6A, bottom side Yellow 4B; florets lighten to Yellow 2C near base blending to Yellow 8B at top, bottom side Yellow 3A.

*Disc*.—Flat becoming rounded, becoming to 40 mm deep and 55 mm wide with maturity, overall color Yellow 7A.

*Disc florets*.—To about 207 in number, each with 1 pistil and 4 stamen, grow to 27 mm long and 7 mm wide, each with one persistent, very stiff, linear bract (12 mm long with 3 mm Yellow 8B at apex blending to 3 mm Yellow 5C to White 155A at base); showy 3 to 5-lobed corollas to 17 mm long and 7 mm wide, tubular on the bottom with the lobes spread out like a fan, glabrous on both sides; back side Yellow 8C, inside Yellow 3C; pistil 10 mm long, ovary 3.5 mm long, White NN155A, style 5 mm long White 155A, 2-branched stigma spreading 1.5 mm wide, Yellow 11C; stamen 4 mm long and thread-like, anthers 2 mm long and Greyed Purple N187A, filaments 2.3 mm long, White 155A, pollen none.

*Involucral bracts*.—In 4 leafy series, area grows to 30 mm wide and 10 mm deep, lobes lanceolate in shape, reflexed, grow to 9 mm long and 3 mm wide, Green 137B, margins strigose, tip acute, strigose on both sides.

*Receptacle*.—Grows to 15 mm wide and 16 mm deep, White NN155B.

*Bloom period*.—June through October in Canby, Oreg.

*Fragrance*.—Moderate, sweet.

*Lastingness*.—Each inflorescence lasts about two to three weeks in Canby, Oreg.

Seeds: None seen.

*Fertility*.—None.

Disease and pests: No pests or diseases have been observed on plants grown under commercial conditions in Canby, Oreg. No resistances are known.

I claim:

1. A new and distinct *Echinacea* plant as herein illustrated and described.

* * * * *